United States Patent
Kuusela et al.

(10) Patent No.: US 11,278,738 B2
(45) Date of Patent: Mar. 22, 2022

(54) USING ISODOSE SURFACES FOR OPTIMIZING DOSE DISTRIBUTION IN RADIATION TREATMENT PLANNING

(71) Applicant: Varian Medical Systems International AG, Steinhausen (CH)

(72) Inventors: Esa Kuusela, Espoo (FI); Hannu Laaksonen, Espoo (FI); Lauri Halko, Helsinki (FI)

(73) Assignee: Varian Medical Systems International AG, Steinhausen (CH)

( * ) Notice: Subject to any disclaimer, the term of this patent is extended or adjusted under 35 U.S.C. 154(b) by 175 days.

(21) Appl. No.: 16/370,557

(22) Filed: Mar. 29, 2019

(65) Prior Publication Data
US 2020/0306559 A1 Oct. 1, 2020

(51) Int. Cl.
*A61N 5/10* (2006.01)

(52) U.S. Cl.
CPC ......... *A61N 5/1036* (2013.01); *A61N 5/1031* (2013.01); *A61N 5/1045* (2013.01)

(58) Field of Classification Search
CPC .. A61N 5/1045; A61N 5/1031; A61N 5/1043; A61N 5/1036
See application file for complete search history.

(56) References Cited

U.S. PATENT DOCUMENTS

| | | | |
|---|---|---|---|
| 5,373,844 A | 12/1994 | Smith | |
| 2009/0316858 A1 | 12/2009 | Nord | |
| 2014/0275703 A1 | 9/2014 | Sobotta | |
| 2017/0091387 A1* | 3/2017 | Kuusela | ............... A61N 5/1031 |
| 2018/0078792 A1 | 3/2018 | Ollila | |
| 2019/0083814 A1 | 3/2019 | Tailinen et al. | |
| 2019/0247676 A1 | 8/2019 | Peltola et al. | |

OTHER PUBLICATIONS

Chen et al., "Multi Criteria Optimization Informed VMAT Planning", Medical dosimetry, vol. 39, No. 1, 2014, 20 pages.
Djemil, "Pinnacle Auto-Planning", Cleveland Clinic, Apr. 29, 2016, 37 pages.
Monz et al., "Pareto Navigation-Algorithmic Foundation of Interactive Multi-Criteria IMRT Planning", Physics in Medicine and Biology, vol. 53, No. 4, Feb. 21, 2008, pp. 985-998.
International Search Report and Written Opinion from International Application No. PCT/EP2020/057847 dated May 12, 2020; 14 pages.

* cited by examiner

*Primary Examiner* — Christine H Matthews
*Assistant Examiner* — Joshua Daryl D Lannu

(57) ABSTRACT

Cost functions and cost function gradients for use in radiation treatment planning can be computed based on an approximation of an "isodose" surface. Where a clinical goal is expressed by reference to a threshold isodose surface, a corresponding cost function component can be defined directly by reference to that isodose surface, and a corresponding contribution to the cost function gradient can be approximated by identifying voxels that are intersected by the threshold isodose surface and approximating the gradient of the dose distribution within each such voxel.

18 Claims, 10 Drawing Sheets

USING ISODOSE SURFACES FOR OPTIMIZING DOSE DISTRIBUTION IN RADIATION TREATMENT PLANNING

BACKGROUND

The present disclosure relates generally to treatment planning for radiation therapy and more specifically to techniques for optimizing dose distribution in radiation treatment planning.

In general, radiation therapy consists of the use of ionizing radiation to treat living tissue, usually tumors. Many different types of ionizing radiation are used in radiation therapy, including high-energy x-rays, electron beams, and proton beams. The process of administering radiation therapy to a patient can be similar across different types of radiation. Typically, an external-beam radiation treatment system is used. Such systems provide a linear accelerator that produces a beam of the desired type at a beam source and collimators including a multileaf collimator (MLC) to shape the beam that emerges from the beam source. The beam delivery system (including the beam source and collimators) is generally mounted on a movable gantry that can be moved around a treatment couch on which a patient is placed, allowing the radiation beam to be delivered from different angles relative to the patient.

Systems of this kind are used for various treatment options. One option is intensity-modulated radiotherapy (IMRT), in which the beam source is positioned at a desired angle, and the MLC is modulated to control the dose received by different tissues. During a treatment session, the beam source and/or the MLC may be repositioned, allowing radiation to be delivered from different angles. In IMRT, the beam source remains stationary while radiation is being delivered. Another treatment option is volumetric modulated arc therapy (VMAT), in which the beam source traverses an arc around the patient while delivering radiation. In both IMRT and VMAT, the overarching goal is to deliver a therapeutically effective dose of radiation (typically a high and uniform dose) to a target volume (typically a tumor) within the patient's body while minimizing the dose delivered to surrounding tissues (in particular, healthy organs or tissues that may be located close to the target volume).

Effective radiation therapy requires treatment planning to determine machine parameters that will optimally achieve the overarching goal. In the case of IMRT, a treatment plan may specify machine parameters such as positions of the beam source and collimators (including MLC leaf settings), beam intensity (e.g., dose rate), and duration of exposure (also referred to as "beam-on time"); the plan may include multiple control points, each defined by a set of machine parameters. In the case of VMAT, a treatment plan may specify all of the same machine parameters as in IMRT, plus additional parameters defining an arc to be traversed and in some instances speed of traversing the arc. During treatment, a treatment plan can be used to control operation of the radiotherapy system, and operating the radiotherapy system according to the treatment plan results in delivering a desired dose distribution to the patient.

Treatment planning is usually approached via the "inverse" problem of determining the optimal combination of machine parameters—such as beam intensity, beam shaping, beam direction(s), exposure duration—to deliver a desired total radiation dose to the target volume (or multiple target volumes) while minimizing the dose delivered to nearby organs or tissues (often referred to as "organs at risk," or "OAR"). The desired radiation doses can be expressed as a set of treatment objectives, and a cost function can be defined to quantify a difference between a predicted radiation dose and the set of treatment objectives. This cost function allows a practitioner to compare different treatment options.

SUMMARY

Among the challenges of treatment planning is defining a cost function. Typically, the cost function is defined based on a dose volume histogram ("DVH") that summarizes three-dimensional (3D) dose distributions in a graphical format, showing what fraction of a volume of interest (e.g., a target volume or an OAR) receives a given dose or what fraction of a volume of interest receives at least a given dose. A DVH, however, offers limited information about how the dose is distributed within the volume of interest.

Certain embodiments of the present invention relate to techniques that can be used to define cost functions (and/or cost function gradients) for use in radiation treatment planning based on an approximation of an "isodose" surface. It is assumed that radiation dose is a continuous function of position in 3D space. An isodose surface can be defined as the locus of points such that each point receives the same dose (e.g., 30 Gray, 40 Gray, or any other particular dose). A clinical goal can be expressed by reference to an isodose surface, e.g., by specifying that a particular volume should receive at least a threshold dose (or not more than a threshold dose), by specifying that the volume enclosed by a particular isodose surface (i.e., the volume receiving at least the threshold dose) should meet some upper (or lower) limit, or by specifying that a particular isodose surface should conform to the shape of a target volume or be located at least a minimum distance from an organ at risk. Where a clinical goal is expressed by reference to a threshold isodose surface, a corresponding cost function component can be defined directly by reference to that isodose surface, and a corresponding contribution to the cost function gradient (also referred to herein as a "gradient element") can be approximated by identifying voxels that are intersected by the threshold isodose surface and approximating the gradient of the dose distribution within each such voxel. Cost function components and gradient elements computed in this manner can be used, e.g., in a multicriteria optimization (MCO) process for radiation treatment planning.

Some embodiments relate to computer-implemented methods for radiation treatment planning. For example, a set of clinical goals can be received, and the set of clinical goals can include at least a first clinical goal that is expressed with reference to a threshold isodose surface corresponding to a threshold dose. (It should be understood that any or all of the clinical goals can be expressed with reference to a threshold isodose surface, with different clinical goals potentially referencing different isodose surfaces.) A cost function (for use in multicriteria optimization) can be defined such that the cost function has a cost function component corresponding to each clinical goal in the set of clinical goals. In particular, a first cost function component corresponding to the first clinical goal can be defined based directly on the threshold isodose surface. For each treatment plan in a set of a set of candidate treatment plans, the cost function and a cost function gradient can be computed; in some embodiments, the cost function gradient has a gradient element corresponding to each cost function component. For the first cost function component, computing the gradient element can be based on per-voxel approximation of the threshold isodose surface. For instance, a set of voxels of interest can be identified such that the set of voxels of interest includes at least some voxels that are intersected by the threshold isodose surface; in some embodiments, the set of voxels of interest includes only voxels that are intersected by the threshold isodose surface. Voxels that are intersected by the threshold isodose surface can be identified, e.g., by determining a dose at each corner point of the voxel and comparing the doses at the corner point to the threshold dose associated with the threshold isodose surface. For each voxel of interest, a gradient of a dose distribution can be computed, e.g., by linear interpolation or other interpolation between the doses determined at the corner points, and a local contribution to the gradient element can be computed based at least in part on the gradient of the dose distribution. In some embodiments, the local contribution to the gradient element can be based on change in a volume of the voxel inside the threshold isodose surface that results from changing the dose by a specified small amount. Cost function minimization (e.g., multicriteria optimization) can be performed using the cost function and the cost function gradient, and an optimized treatment plan can be generated based on a result of the cost function minimization.

The following detailed description, together with the accompanying drawings, will provide a better understanding of the nature and advantages of the claimed invention.

DEFINITIONS

Figure 1:
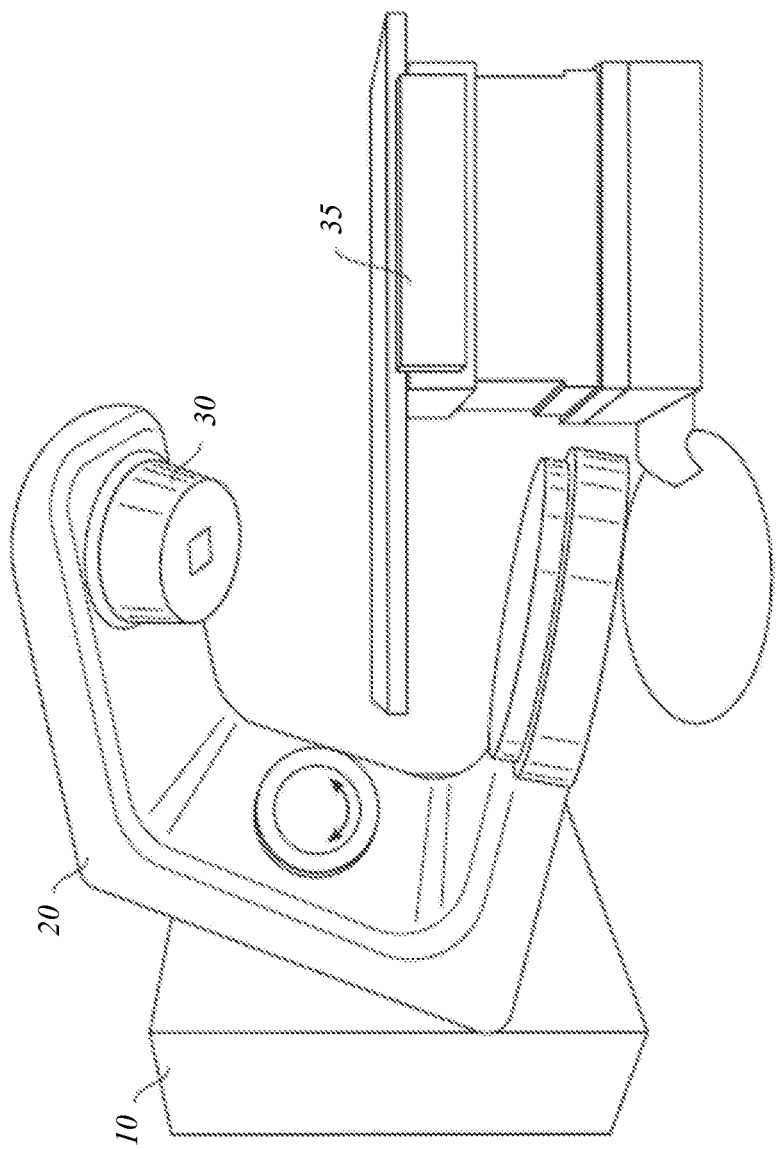
FIG. 1 shows a perspective view of a radiation treatment system that may be used in connection with an embodiment of the present invention.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" refer to tissue intended to receive a therapeutic prescribed dose. The irradiated volume is generally larger than the target volume and may include organs or tissues that are not intended to receive a therapeutic dose. Such organs or tissues are sometimes referred to as "organs at risk" (OAR).

A "dose distribution" provides information about the variation in the dose of radiation with position. A dose distribution can be represented in many formats, e.g., a dose volume histogram (DVH) or a dose matrix. A DVH can summarize three-dimensional (3D) dose distributions in a graphical format, e.g., where the horizontal axis is the dose (e.g., in units of grays (Gy)) absorbed by a particular volume or structure (which can be the target volume, an OAR, or any other well-defined volume) and the vertical axis is a volumetric percentage. In a differential DVH, the height of a bar at a particular dose indicates the volumetric percentage of the volume in question that receives the particular dose. In a cumulative DVH, the height of a bar at a particular dose represents the volumetric percentage of the volume in question that receives greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can show the dose that each part of the body receives.

A "dose prediction model" receives patient data and machine parameters and outputs a dose distribution that is predicted to be obtained. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test radiation treatment plans whose dose distribution has been determined via other means (e.g., by optimizing a cost function). For example, the accuracy can be determined based on how well the model predicts the actual dose distributions obtained by optimizing a cost function. Examples of techniques for creating and selecting a dose prediction model for a treatment plan are described in U.S. Pat. No. 9,827,445, issued Nov. 28, 2017.

A "radiation treatment plan" (also referred to as a "treatment plan" or "plan") can include a particular dose distribution or set of radiation fields that provides a particular dose distribution, machine parameters for achieving the dose distribution for a given patient, and information about the given patient. Examples of radiation treatment plans and generation thereof are described in U.S. Pat. No. 7,796,731, issued Sep. 14, 2010; U.S. Pat. No. 7,801,270, issued Sep. 21, 2010; U.S. Pat. No. 9,827,445, issued Nov. 28, 2017; and U.S. Pat. No. 10,166,406, issued Jan. 1, 2019.

"Monitor unit" (MU) is a measure of machine output from a clinical accelerator for radiation therapy such as a linear accelerator. Monitor units are measured by monitor chambers, which are ionization chambers that measure the dose delivered by a beam and are built into the treatment head of radiotherapy linear accelerators. Linear accelerators are calibrated to give a particular absorbed dose under particular conditions, although the definition and measurement configuration will vary between centers.

Two common definitions of monitor units are: (1) the monitor chamber reads 100 MU when an absorbed dose of 1 gray (100 rads) is delivered in the centerline of the field to a point at the depth of maximum dose in a water-equivalent phantom whose surface is at the isocenter of the machine (e.g., at 100 cm from the source for a typical machine) with a field size at the surface of 10 cm×10 cm; and (2) the monitor chamber reads 100 MU when an absorbed dose of 1 Gy (100 rad) is delivered to a point at a given depth in the phantom with the surface of the phantom positioned so that the specified point is at the isocenter of the machine and the field size is 10 cm×10 cm at the isocenter.

Some linear accelerators are calibrated using source-to-axis distance (SAD) instead of source-to-surface distance (SSD), and calibration (monitor unit definition) may vary depending on hospital custom. Early radiotherapy was performed using "constant SSD" treatments, and so the definition of monitor unit was adopted to reflect this calibration geometry. Modern radiotherapy is performed using isocentric radiation treatment plans, so newer definitions of the monitor unit are based on geometry at the isocenter based on the source-to-axis distance (SAD).

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, the gantry angle, the collimator angle, and the position of each MLC leaf. The term "control point" refers to a parametrical point of a radiation treatment field that includes spatial information about the treatment axes and may also specify collimator settings, beam intensity or dose rate (e.g., using MU count and/or the related concept of the meterset weight), and/or speed of motion of the beam source (including a speed of a movable gantry supporting the beam source).

DETAILED DESCRIPTION

1. Radiation Therapy Systems

External beam therapy (EBT), also called external radiation therapy, is a method for delivering a beam or several beams of photons (e.g., x-rays) or other particles (e.g., protons, electrons) to a patient's tumor. Beams are generated outside the patient and are targeted at the tumor site.

Figure 2:
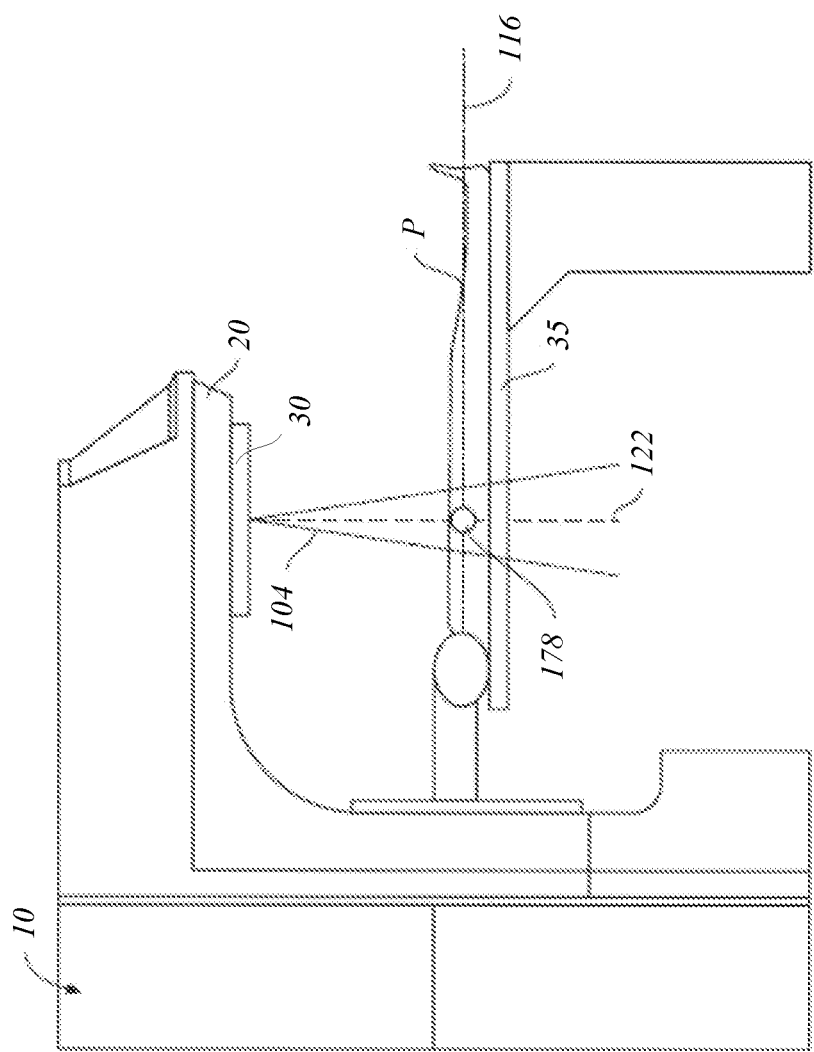
FIG. 2 shows a side view of the radiation treatment system of FIG. 1.

FIGS. 1 and 2 depict a radiation treatment system 100 that may be used in connection with an embodiment of the present invention. FIG. 1 shows a perspective view of radiation treatment system 100 (in this case incorporating a linear accelerator). Radiation treatment system 100 may be capable of generating either a particle beam (e.g., electrons or protons) or a photon beam (e.g., x-rays) for use in the radiotherapy treatment of a patient on a treatment couch 35. For purposes of the present description, x-ray irradiation will be assumed. However, it will be appreciated by those skilled in the art that the same principles apply to other systems, including electron beam systems and heavy-ion (e.g., proton) beam systems.

Stand 10 supports a rotatable gantry 20 with a treatment head 30. Next to stand 10 there is arranged a control unit (not shown) which includes control circuitry for controlling the different modes of operation of radiation treatment system 100. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

FIG. 2 shows a somewhat more detailed side view of radiation treatment system 100. A patient P is shown lying on treatment couch 35. X-rays formed as described above are emitted from the metal target in treatment head 30 in a divergent beam 104. Typically, a patient plane 116, which is perpendicular to the page in FIG. 2, is positioned about one meter from the x-ray source (e.g., the metal target), and the axis of gantry 20 is located in patient plane 116, such that the distance between the target in treatment head 30 and isocenter 178 remains constant when gantry 20 is rotated. Isocenter 178 is a point located at the intersection between patient plane 116 and the central axis of beam 122. Patient P can be positioned on treatment couch 35 such that a treatment volume to be irradiated is located about isocenter 178.

Figure 3:
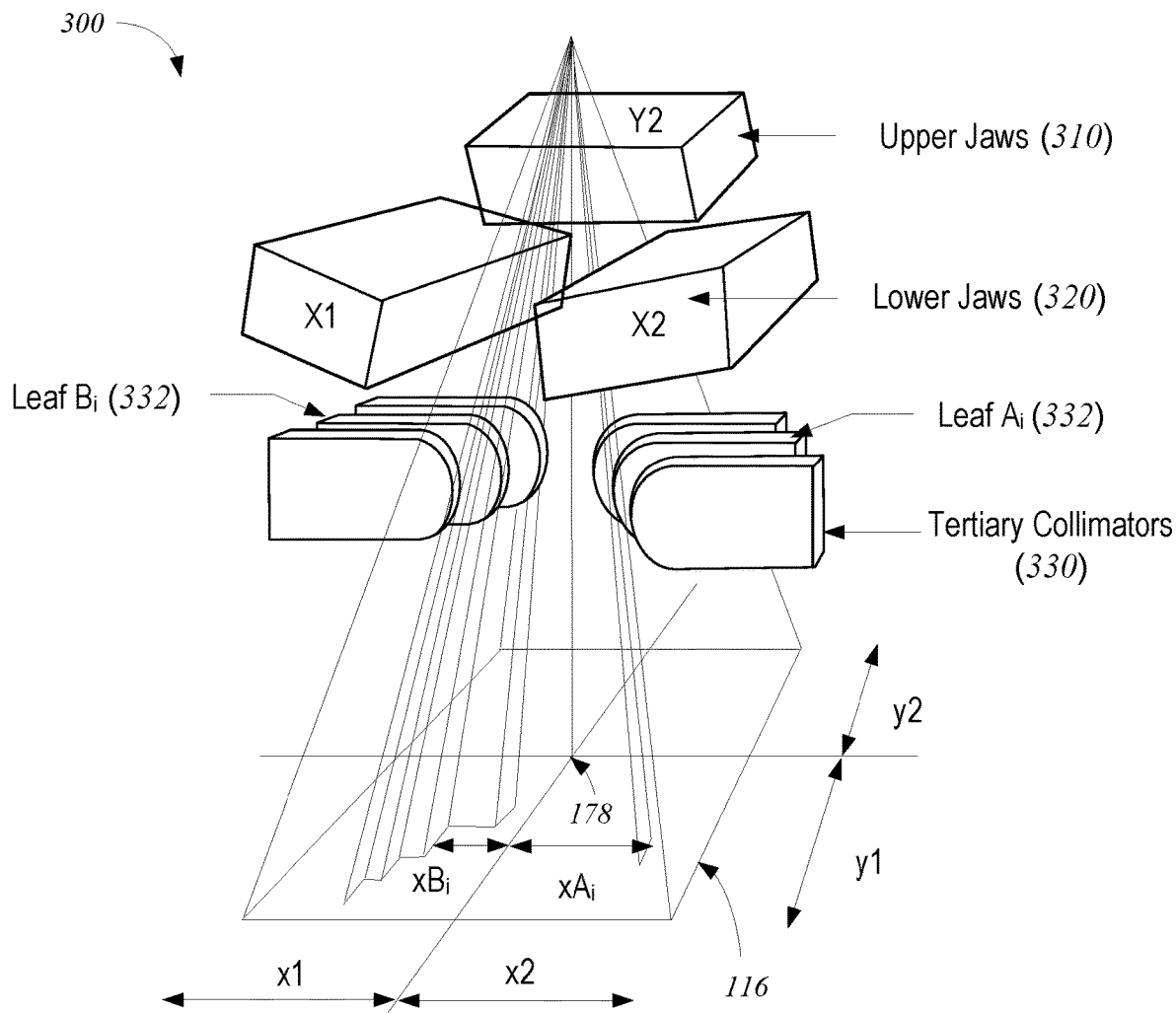
FIG. 3 shows schematically a photon collimation system that may be included in the radiation treatment system of FIG. 1.

In some embodiments, the beam can be shaped, e.g., using configurable collimators, to optimize the dose distribution to selectively target a tumor or other diseased tissue. FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in patient plane 116 and the location of isocenter 178 are indicated. Upper jaws 310, lower jaws 320, and leaves 332 of MLC 330 are made at least partially of an x-ray blocking material and are positioned in treatment head 30 (shown in FIG. 2) to define the width of the x-ray beam at patient plane 116. Typically, jaws 310 and 320 are moveable and, when fully open, define a maximum beam width of about 40 cm×40 cm at patient plane 116. MLC 330 is positioned at the exit of treatment head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
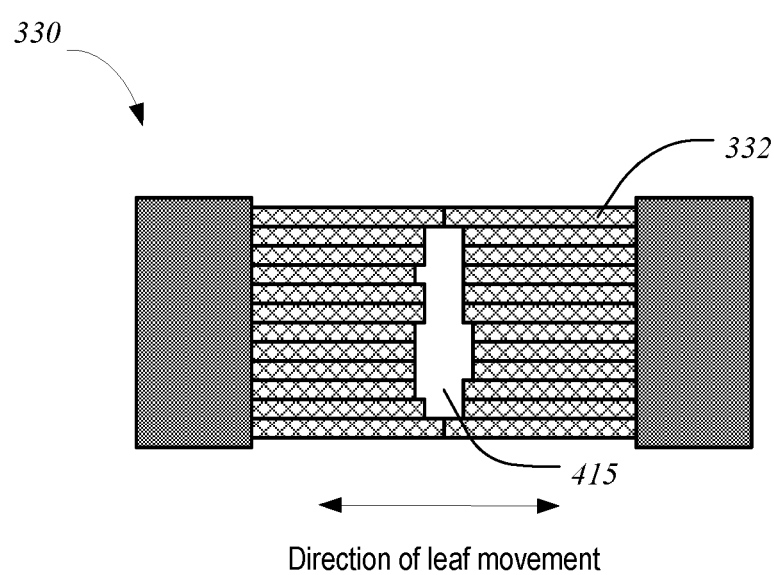
FIG. 4 shows an exemplary multileaf collimator plane that may be used in the photon collimation system of FIG. 3.

FIG. 4 shows an exemplary MLC plane having a plurality of leaves 332, arranged in opposing pairs, and an aperture 415 created by selected leaf movements. Radiation passes through and is shaped by aperture 415. Thus, MLC 330 can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to isocenter 178 in the treatment path of the x-ray beam, is defined by jaws 310 and 320, the leaf sequence of MLC 330, and the collimator angle, i.e., the angle at which MLC 330 sits in treatment head 30. In some embodiments, the position of jaws 310 and 320, the leaf sequence of MLC 330, and the collimator angle are all controllable machine parameters; in other embodiments, some of these parameters may be fixed. Examples of an MLC and leaf sequence optimization are described in U.S. Pat. No. 7,796,731, issued Sep. 14, 2010.

Figure 5:
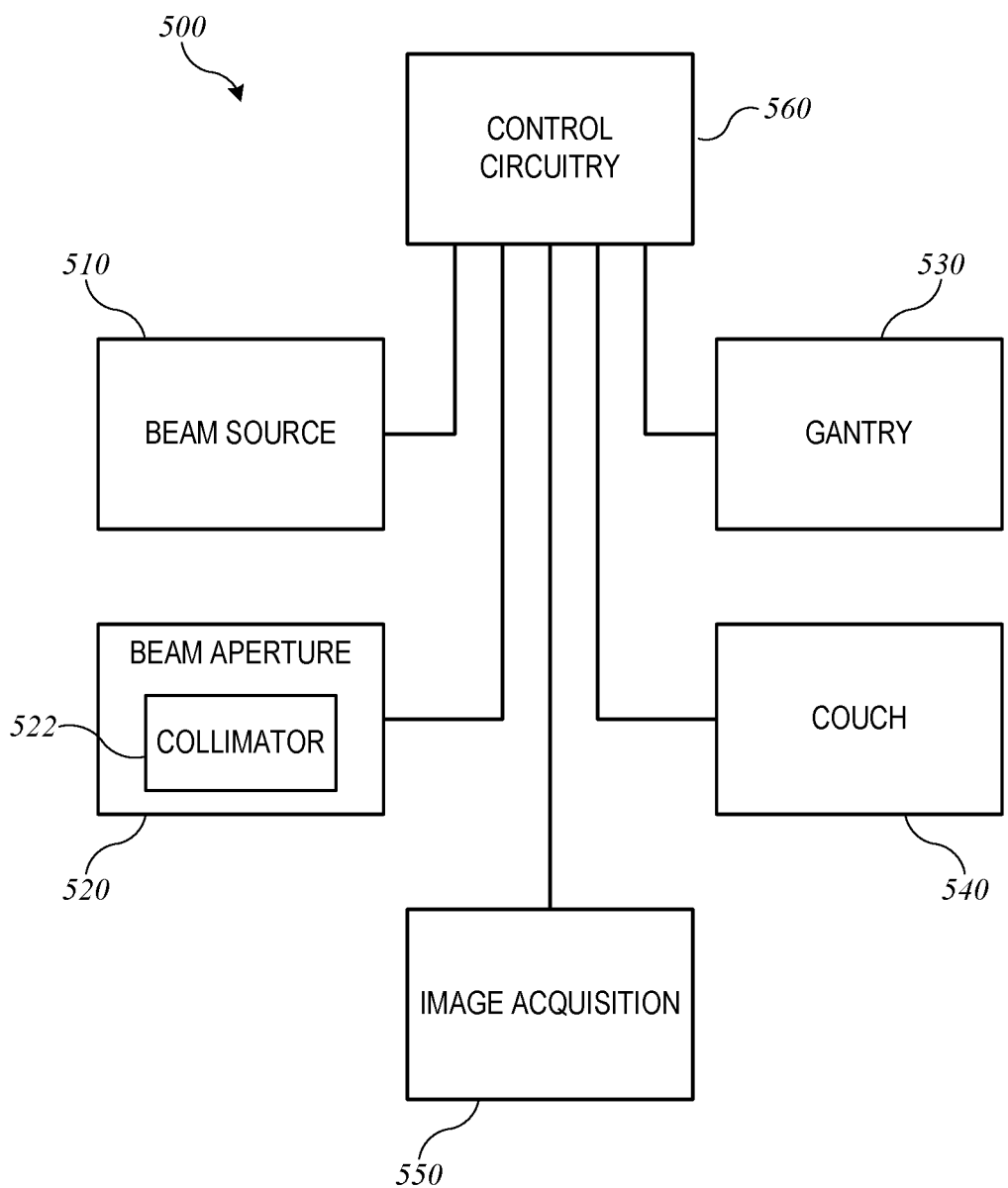
FIG. 5 shows a block diagram of an external-beam radiation treatment system that may be used in connection with the present invention.

FIG. 5 shows a block diagram of an external-beam radiation treatment system 500 implementing radiation treatment system 100 of FIGS. 1 and 2. Radiation treatment system 500 includes a beam source 510, a beam aperture 520, a gantry 530, and a couch 540. Beam source 510 is configured to generate a beam of therapeutic radiation. This beam of radiation may include x-rays, particles, or the like. Beam aperture 520 includes an adjustable multi-leaf collimator (MLC) 522, which can be an implementation of MLC 330 described above, for spatially filtering the radiation beam. Couch 540, which can be an implementation of treatment couch 35 of FIGS. 1 and 2, is configured to support and position a patient during treatment. Couch 540 may have six degrees of freedom (the translational offsets X, Y, and Z, and the rotation, pitch, and yaw), which may be treated as machine parameters.

Gantry 530, which can be an implementation of gantry 20, houses beam source 510 and beam aperture 520. Gantry 530 can be movable, e.g., rotatable, around a fixed axis, and volumetric modulated arc therapy ("VMAT") treatment can be performed by rotating gantry 530 while beam source 510 is delivering beam. The arc to be traversed (e.g., starting and ending points) and/or speed of traversal can be treated as additional machine parameters.

In some embodiments, beam source 510 can be configured to generate imaging radiation as well as therapeutic radiation. Accordingly, radiation treatment system 500 may also include an image acquisition system 550 that comprises one or more imaging detectors mounted to gantry 530 (e.g., on an arm opposite beam aperture 520).

Radiation treatment system 500 further includes control circuitry 560 for controlling the operation of beam source 510, beam aperture 520, gantry 530, couch 540, and image acquisition system 550. Control circuitry 560 may include hardware, software, and memory for controlling the operation of these various components of radiation treatment system 500. Control circuitry 560 can comprise a fixed-purpose hard-wired platform or can comprise a partially or wholly-programmable platform. Control circuitry 560 can be configured to carry out various steps, actions, and other functions described herein. In some embodiments, control circuitry 560 may include a memory for receiving and storing a radiation treatment plan that defines the spatial points or control points of one or more treatment fields. Control circuitry 560 may then send control signals to the various components of radiation treatment system 500, such as beam source 510, beam aperture 520, gantry 530, and couch 540, to execute the radiation treatment plan. In some embodiments, control circuitry 560 may include an optimization engine to determine a radiation treatment plan; in other embodiments, an optimization engine can be provided in a separate computer system that delivers a radiation treatment plan to control circuitry 560 via a network interface or computer-readable storage medium.

2. Treatment Planning Overview

For therapeutically effective use of radiation treatment system 100 (or similar systems), it is generally desirable to develop a treatment plan prior to exposing a patient to radiation. During treatment planning, a medical practitioner or other user of a treatment planning system or method identifies a set of clinical goals specifying desired limits on the radiation dose to be delivered to various regions of interest within the irradiation volume. The regions of interest generally include one or more target structures (which can include tumors or other tissue to be treated) and one or more organs at risk (OAR) (which can include any healthy tissues or structures that may be near enough to a target structure to be subjected to at least some radiation). By way of example, if the target structure is a prostate tumor, associated OAR may include the bladder, spinal cord, and rectum. For a target structure, a clinical goal is generally defined as a uniform and therapeutically effective ("high") dose across the entire structure. For an OAR, a clinical goal is generally defined with reference to an upper limit on the dose, with the goal of avoiding or minimizing radiation damage to healthy tissue; the particular upper limit generally depends on the tissue type. Treatment planning involves identifying a set of treatment fields (and corresponding machine parameter settings to produce the fields) that satisfy the clinical goals. Depending on implementation, the treatment fields may include stationary treatment fields (where the direction and distance to the treatment target is fixed during beam-on) and/or dynamic treatment fields (where the direction of incidence to the treatment target changes during continuous irradiation).

In practice, the clinical goals may conflict with each other, in the sense that not all of the clinical goals can be satisfied by any particular treatment plan (i.e., set of treatment fields). Where clinical goals conflict, multicriteria optimization (MCO) can be used to optimize the treatment plan. Based on the clinical goals, a generalized cost function can be defined. For instance, a desired treatment outcome (i.e., an outcome that meets all of the clinical goals) can be defined as a vector in a multidimensional space, with each component of the vector corresponding to a dose delivered to a particular volumetric element (voxel) within the patient's body. A cost function is defined to quantify a distance (in the multidimensional space) between the desired outcome and an alternative outcome (e.g., the predicted outcome of a particular treatment plan). Euclidean or other distance metrics can be used, and different components of the outcome vector may be assigned different weights in the cost function. An optimized solution can be identified by finding a treatment plan for which the outcome minimizes the cost function. For instance, a dose prediction model can be used to generate alternative outcomes for various combinations of adjustable machine parameters (e.g., beam intensity, beam aperture, MLC leaf sequence, duration of exposure, relative position of beam and patient), and the cost function can be computed for various alternative outcomes. A minimum value of the cost function can be found, e.g., using a gradient descent method. For example, the cost function gradient can be used to identify a direction of steepest descent; a fixed step size can be followed in that direction; and the cost function can be recomputed at the new location. This process can be iterated until convergence (e.g., defined as minimal change in the cost function over some number of iterations). Other techniques, such as a conjugate gradient, Newton or quasi-Newton method can be used to determine the search direction for an iteration.

The particular set of treatment fields that yields a cost-function value closest to the minimum (relative to other modeled sets of treatment fields) can be identified as an optimized treatment plan. In some implementations, two (or more) modeled sets of treatment fields can be combined (e.g., using interpolation) to expand the space of possible sets of treatment fields. Information about the optimized treatment plan can be presented to the user, e.g., in a display that includes data about dose distribution, such as a DVH for various volumes of interest and/or a color-coded image showing the dose at various points in space. In some instances, the user can iterate on the planning process, e.g., by adjusting weights in the cost function and/or by adjusting the clinical goals. Once a final optimized treatment plan is determined, adjustable machine parameters that produce the set of treatment fields corresponding to the final optimized treatment plan can be provided in machine-readable form to a radiation treatment system 100 (usually at a later time), which can be operated in accordance with the plan to deliver a radiation treatment to a patient.

3. Cost Function Components Based on Isodose Surfaces

Clinical goals for radiation treatment generally relate to providing a high dose of radiation within a target volume while keeping the dose to surrounding tissues sufficiently low. The specific clinical goals for a particular treatment planning process quantify the desired dose limits. For example, a user may specify as a clinical goal a volume limit, e.g., that less than 30% of a target volume should receive a dose greater than 50 Gy. As another example, a user may specify as a clinical goal a dose limit, e.g., that the dose in the hottest 40% of a target volume should be at least 30 Gy. As yet another example, a user may specify that an isodose surface corresponding to a prescription dose should conform as closely as possible to the target volume, or that the volume receiving 50% (or more) of the prescription dose be as small as possible.

Figure 6:
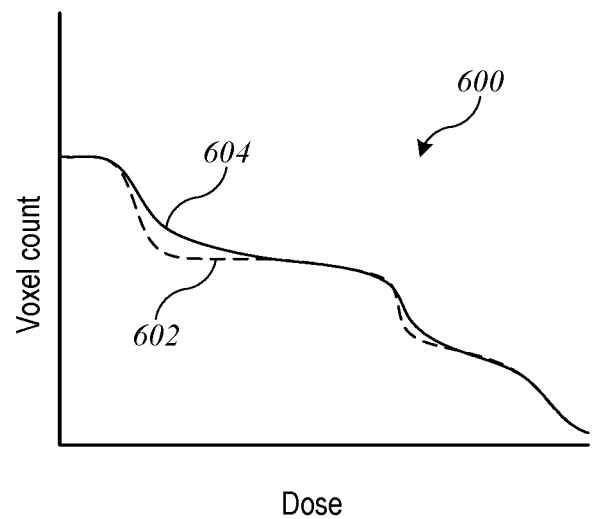
FIG. 6 shows an example of a dose volume histogram that can be used in treatment planning.

In conventional treatment planning processes, clinical goals such as these examples are restated as objectives for a dose volume histogram (DVH), from which a cost function can be computed. By way of illustration, FIG. 6 shows an example of a DVH 600 in which the x axis shows dose values and the y axis shows a count of voxels (volume elements of uniform size) that will receive at least the corresponding dose value. A DVH such as DVH 600 can be generated for a particular volume of interest (e.g., a target volume or an OAR). Dashed line 602 represents an objective for the DVH, and solid line 604 corresponds to a predicted DVH outcome for a modeled treatment plan. Where lines 602 and 604 deviate from each other, cost is incurred, and a component of the cost function can be defined based on the amount by which lines 602 and 604 deviate. In some instances, a generalized Equivalent Uniform Dose (gEUD) technique is used to provides a single value summarizing DVH curve information, which can be used in cost function optimizations. However, while DVH 600 is correlated with the actual clinical objective, the correlation is inexact, which implies that a treatment plan determined by optimizing a cost function based (in part) on DVH 600 may not be the actually optimal plan (i.e., the plan that, when used in treatment, delivers the optimal radiation distribution).

Some embodiments described herein allow cost functions to be defined using clinical goals expressed by reference to isodose surfaces. It is assumed that the distribution of radiation dose is a smoothly varying function of position, such that a locus of points for which a dose has a particular level (e.g., 50 Gy) defines a surface in 3D space; such surfaces are referred to herein as "isodose surfaces."

Figure 7:
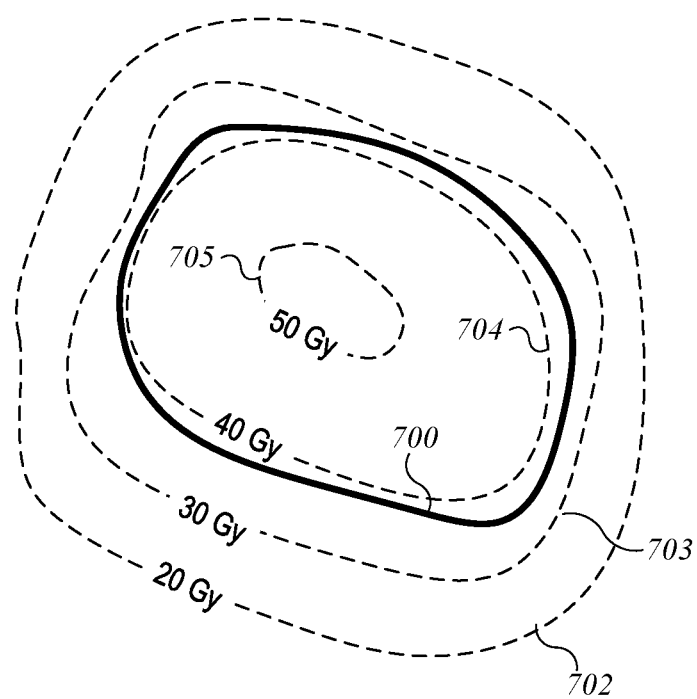
FIG. 7 shows a simplified illustration of isodose surfaces that may be associated with a treatment plan according to an embodiment of the present invention.

FIG. 7 shows a simplified illustration of isodose surfaces that may be associated with a treatment plan. The view shown in FIG. 7 should be understood as a two-dimensional (2D) cross section of a three-dimensional (3D) region. A target volume 700 is identified by a solid line. Target volume 700 may represent, e.g., a tumor site or other target for radiation treatment. Broken lines 702, 703, 704, 705 represent isodose surfaces corresponding to doses of 20 Gy, 30 Gy, 40 Gy, and 50 Gy (as indicated by the labels). In this example, 40-Gy isodose surface 705 is just inside the outer surface of target volume 700, which indicates that most (but not all) of target volume 700 will receive a dose of at least 40 Gy, and a smaller portion near the center will receive at least 50 Gy.

Clinical goals, such as the examples given above, can be expressed directly in terms of isodose surfaces. For example, a clinical goal specified as a volume limit (e.g., that less than 30% of a target volume should receive a dose greater than 50 Gy) can be expressed as "the volume inside the 50 Gy isodose surface should be less than 30% of the target volume." As another example, a clinical goal specified as a dose limit (e.g., that the dose in the hottest 40% of a target volume should be at least 30 Gy) can be expressed as "the volume inside the 30 Gy isodose surface should be at least 40% of the target volume." As yet another example, a clinical goal specifying conformity of an isodose surface (at a prescribed dose) to a target volume is directly expressed by reference to the isodose surface corresponding to the prescribed dose.

Some embodiments described herein support defining a cost function (or at least one component of a cost function) directly based on the difference between a clinical goal expressed as an isodose surface and an isodose surface of a model-generated outcome. A cost function defined in this manner can be used to find an optimized solution in the same manner as a conventionally-defined cost function (e.g., a cost function defined by reference to a DVH as described above).

By way of illustration, three examples of using isodose surfaces to define a cost function component corresponding to a particular clinical goal will be described. It should be understood that other types of clinical goals may also be amenable to defining cost function components based on isodose surfaces.

As a first example, a cost function component corresponding to a clinical goal expressed as a volume limit can be defined based on an isodose surface. Such goals are typically specified as "volume receiving a dose greater than d is less than y % of the volume of the relevant anatomical structure" (which may include, e.g., a target volume and/or an OAR). For instance, d might be 50 Gy and y % might be 30%. A cost function component $C_v$ corresponding to a volume-limit clinical goal can be specified as:

$$C_v = \begin{cases} w_v(V_d - V_d^G)^2 & \text{if } V_d > V_d^G \\ 0 & \text{otherwise} \end{cases}, \quad (1)$$

where $V_d$ is the volume receiving a dose of at least d for a given plan, $V_d^G$ is the specified upper limit on the volume receiving that dose (e.g., y % of the total volume of the relevant anatomical structure), and $w_v$ is a weight parameter that is set as part of the multi-component optimization process. $V_d$ can be computed from the isodose surface as $$V_d = \int dV \theta(D(x) - d), \quad (2)$$

where $D(x)$ is the dose distribution field (i.e., a function defining the dose at location x in 3D space) and $\theta(\cdot)$ is the Heaviside step function, which takes the value 1 when the argument is positive and 0 otherwise. The integral is taken over the whole volume of the relevant anatomical region. Note that Eq. (2) corresponds to the volume inside the isodose surface for dose d.

As a second example, a cost function component corresponding to a clinical goal expressed as a minimum dose covering a target structure can be computed based on an isodose surface. Such goals are typically specified as "the entire target structure should receive at least dose d." For instance, d might be 40 Gy. A cost function component $C_m$ corresponding to a minimum-dose treatment goal can be specified as:

$$C_m = w_m \int dV \, \theta((D(x)-d) \times \sigma_{target}(x)), \quad (3)$$

where d is the minimum dose, $w_m$ is a weight parameter that is set as part of the multi-component optimization process, and $\sigma_{target}(x)$ is a signed distance function from the target volume surface (negative inside). Various distance metrics (e.g., Euclidean distance) can be used.

As a third example, a cost function component corresponding to a given isodose surface drawn by the user can be defined. In some embodiments, a cost function component $C_q$ corresponding to modification of an isodose line for dose d can be specified as:

$$C_q = w_q \int dV \theta(D(x)-d) \times S(x-x_0), \quad (4)$$

where $w_q$ is a weight parameter that is set as part of the multi-component optimization process the stencil function $S(x-x_0)$ is nonzero only in the vicinity of the user-specified location $x_0$ of the isodose surface.

4. Gradient of Cost Function Based on Isodose Surfaces

In practice, numerical optimization based on cost functions having components based on an isodose surface (e.g., the examples in Eqs. (1)-(4)) is challenging, in part because numerical optimization techniques (such as gradient descent methods) rely on the gradient of the cost function. For the Heaviside step function, the gradient is represented by a delta function $\delta(\cdot)$, which is infinite when its argument is zero and zero otherwise; thus, the gradient field is nonzero only in an infinitely small volume. For example, for the cost function component $C_i$ defined by Eqs. (1) and (2), the gradient $\nabla C_i$ has the form:

$$\nabla C_i(x) = 2w_i \delta(D(x)-d) |\nabla D(x)|^{-1}. \quad (5)$$

where $\nabla D(x)$ is the gradient of the dose distribution field $D(x)$.

To provide a numerical solution to Eq. (5) (or other cost-function gradient that includes a gradient of the dose distribution), some embodiments model the dose field by determining the dose at a set of lattice points distributed uniformly in 3D space, e.g., using a dose prediction model of the kind known in the art. In some embodiments, it is assumed that the dose field is a continuously varying function of position whose value can be interpolated (e.g., using linear interpolation) between the lattice points. The contribution to the cost function gradient can be determined by analyzing the effect on the isodose surface at a particular dose d of changing the delivered dose by a small amount.

Figure 8A:
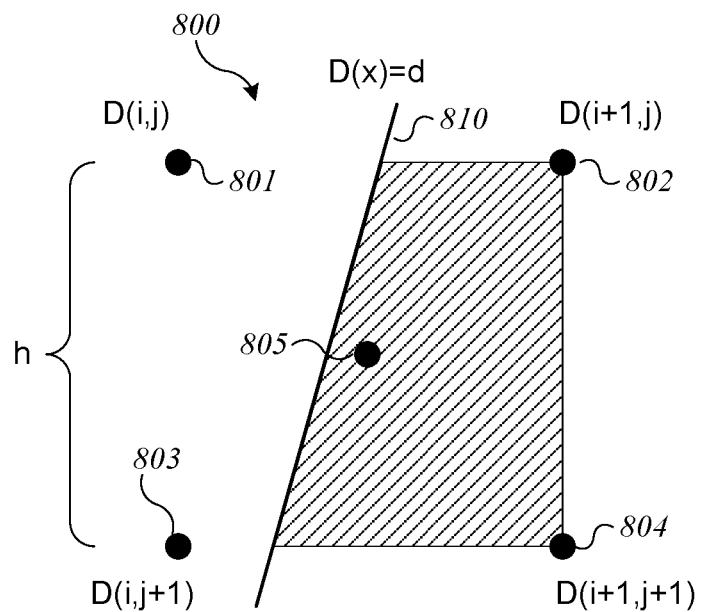
FIGS. 8A and 8B show a simplified example of per-voxel interpolation techniques that can be used in some embodiments of the present invention.
Figure 8B:
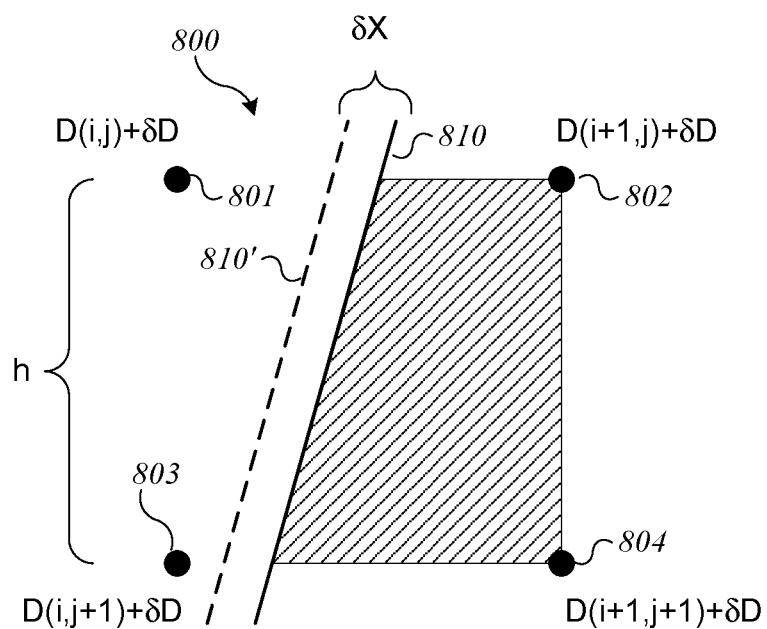

FIGS. 8A and 8B show a simplified example of per-voxel interpolation techniques that can be used in some embodiments. The example is simplified to two dimensions for clarity of illustration; those skilled in the art with access to this disclosure will understand that the interpolation can be performed in three dimensions.

FIG. 8A shows an example of a voxel (or lattice cell) 800 defined by corner points 801, 802, 803, 804, which can be adjacent points in a uniform lattice of sample points. Voxel 800 is shown in two dimensions; however, it should be understood that voxel 800 is three-dimensional (e.g., a cube of dimension h). At each corner point of voxel 800, a dose is computed using a dose prediction model, resulting in dose values D (i, j), D (i, j+1), D (i+1, j), D (i+1, j+1). A "threshold" isodose surface at dose D(x)=d (where dose d is a "threshold" dose, i.e., a dose that is specified in a clinical goal) intersects voxel 800 along line 810, such that the shaded area is inside the threshold isodose surface (i.e., D(x)>d) and the unshaded area is outside (i.e., D(x)<d). The shaded area corresponds to a volume V that is inside the isodose surface; in this example, volume V is a portion of the total volume of voxel 800. The gradient of the dose field, $\nabla D(x)$ is approximated as being uniform across voxel 800 and is computed by interpolation (e.g., linear interpolation) between the corner points. The gradient $\nabla D(x)$ thus determined can be associated with the center point of the voxel (e.g., point 805).

FIG. 8B shows the effect of increasing the dose in the vicinity of voxel 800, e.g., as measured at point 805, by a (specified) small amount $\delta D$. (Although this example shows the change in dose as an increase, the logic described would also apply to decreasing the dose by a specified small amount.) The intersection of voxel 800 with the isodose surface at dose D(x)=d shifts from line 810 to line 810', in this case changing the portion of the voxel volume that is inside the isodose surface from the original volume V to a new volume V'. The effect on the volume inside the isodose surface of changing dose by $\delta D$ can be approximated as $$V' = V + h^2 \delta X, \quad (6)$$

where h is the linear dimension of voxel 800, and $\delta X$ is the distance by which the intersection shifts (e.g., the distance between original isodose line 810 and shifted isodose line 810').

Assuming a constant gradient $\nabla D(x)$, $\delta X$ is given by $$\delta X = \frac{\delta D}{|\nabla D|} \quad (7)$$

and Eq. (6) becomes $$V' = V + h^2 \frac{\delta D}{|\nabla D|}. \quad (8)$$

Eq. (8) shows that the change in V is proportional to the local change $\delta D$ and gradient $\nabla D$ of the dose distribution field D(x). Accordingly, Eqs. (1) and (5) can be used to derive the gradient of the cost function as a function of change in dose. The cost function gradient can be used, e.g., in a gradient descent method, to determine local dose changes that would lead to a smaller cost function. For other cost functions, such as the cost function examples of Eqs. (3) and (4), the same logic applies.

Further, due to the delta function in Eq. (5), it can be assumed that only those voxels that are intersected by the isodose surface of interest (i.e., the surface for which D(x)=d) contribute to the gradient of the cost function. Such voxels can be readily identified by identifying voxels for which at least one corner point has dose less than d and at least one corner point has dose greater than d. This can significantly reduce the computational work required by limiting the number of voxels for which the interpolation procedure is performed.

Figure 9:
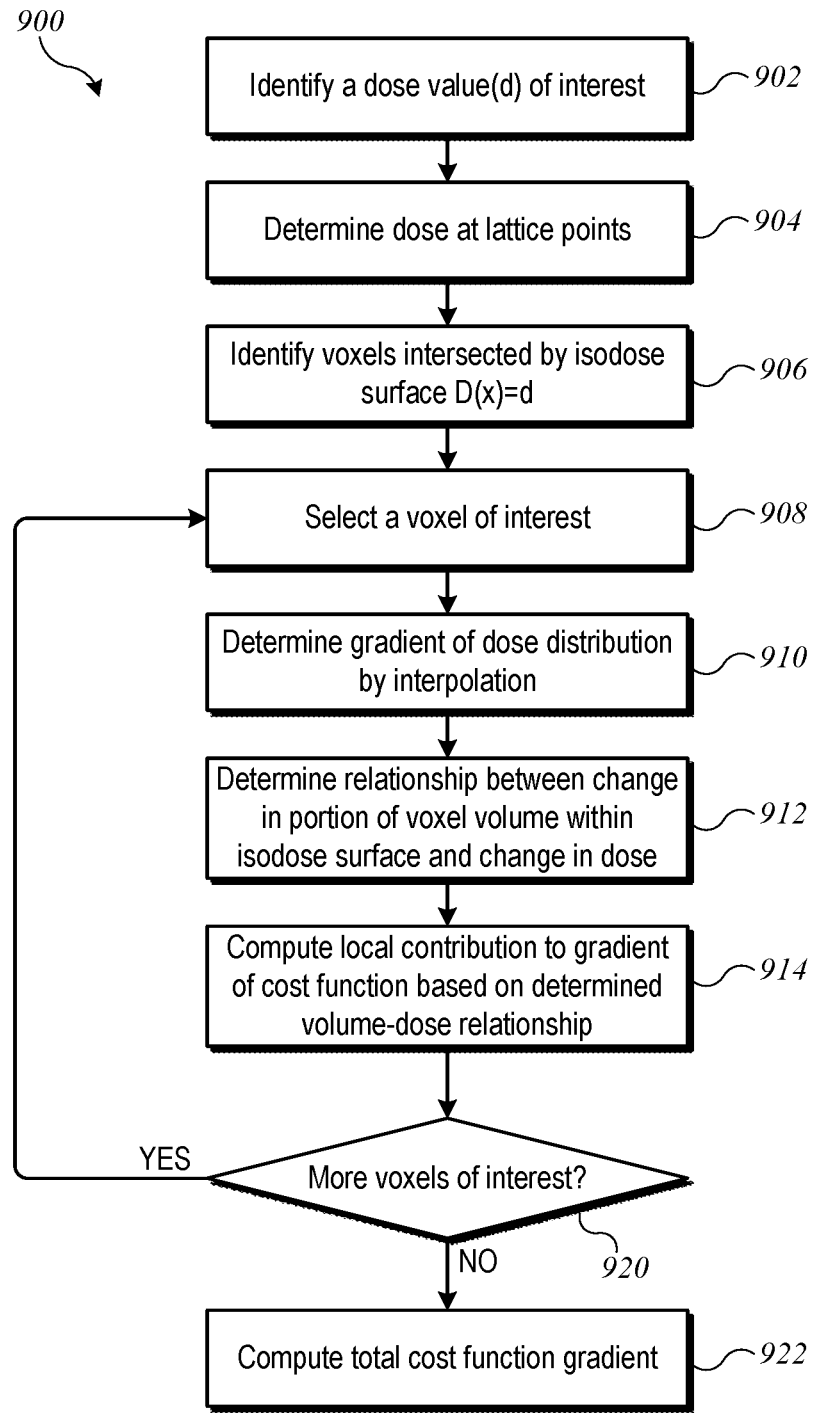
FIG. 9 shows a process that can be used for computing the contribution to a cost function gradient according to an embodiment of the present invention.

FIG. 9 shows a process 900 that can be used for computing the contribution to a cost function gradient for a cost function component expressed in terms of an isodose surface according to an embodiment. In some embodiments, process 900 can be implemented in a computer system used for radiation treatment planning.

At block 902, a dose value of interest (d) is identified. The identification can be based on a clinical goal specified by a user, as in the examples above or other examples.

At block 904, dose is determined at lattice points for a particular treatment plan. The treatment plan can be selected in a manner that depends on the context in which process 900 is being used; an example is described below. The dose at each lattice point can be determined, e.g., using a dose prediction model. The lattice points can be uniformly spaced throughout a volume of interest, e.g., corresponding to an irradiation volume (or any portion thereof). The density of lattice points can be selected as desired. Higher density of lattice points may improve the precision of the dose prediction model but may also increase computation time.

At block 906, voxels in the volume of interest that are intersected by an isodose surface corresponding to $D(x)=d$ are identified. For example, voxels having at least one corner point with $D>d$ and at least one corner point having $D<d$ can be identified. The voxels identified at block 906 are referred to as "voxels of interest."

At block 908, a voxel of interest is selected from the voxels identified at block 906. For the selected voxel, at block 910 a (local) gradient of the dose distribution is determined by interpolation between the corner points as described above. At block 912, a relationship ("volume-dose relationship") between a change in the portion of the voxel volume that lies within the isodose surface and a change in dose can be determined, e.g., using Eq. (8). At block 914, a local contribution to the gradient of the cost function can be computed based on the volume-dose relationship determined for the voxel at block 912.

At block 920, if more voxels of interest remain to be considered, process 900 can return to block 908 to select another voxel of interest. After all voxels of interest have been considered, at block 922, a total cost function gradient (which may be a component of a cost function gradient in the context of MCO) can be computed, e.g., by adding the local contributions for each voxel of interest computed at block 914.

5. Example Treatment Planning Process

Figure 10:
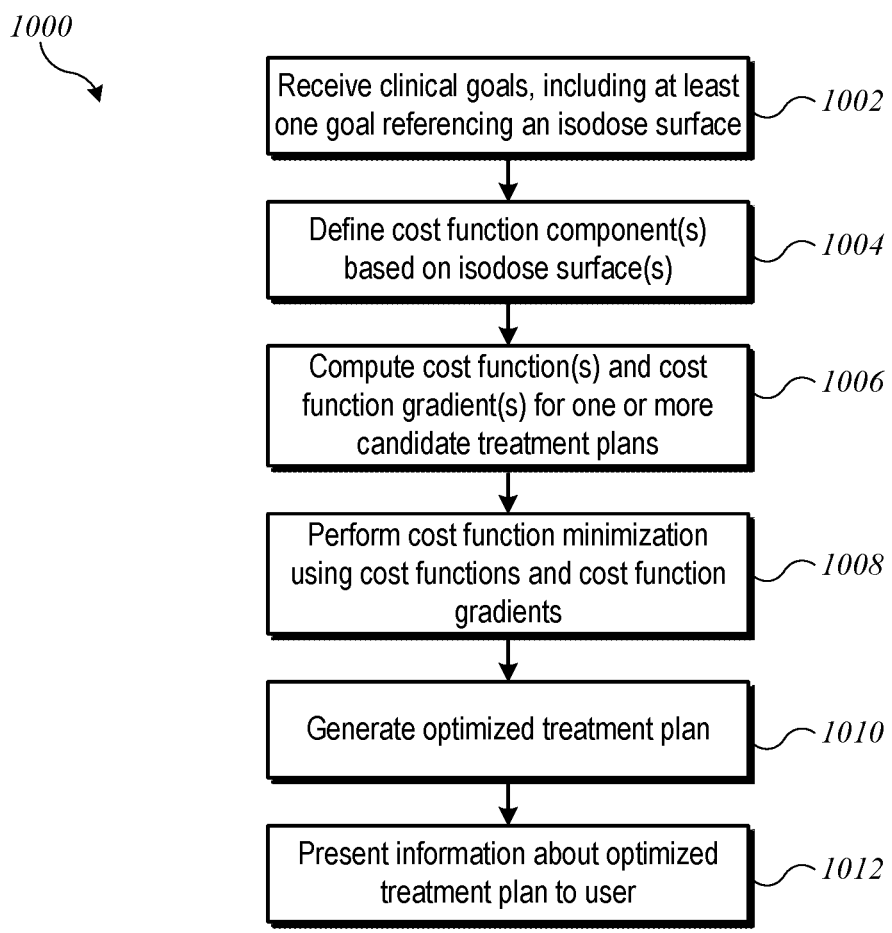
FIG. 10 is an example of a treatment planning process according to an embodiment of the present invention.

Process 900 can be used in a variety of contexts, including an MCO-based radiation treatment planning process. FIG. 10 is an example of a treatment planning process 1000 that incorporates process 900 according to an embodiment. Process 1000 can be implemented in a computer system used for radiation treatment planning. Process 1000 allows a cost function (or a component of a cost function) in MCO-based radiation treatment planning to be defined directly based on the difference between a clinical goal expressed with reference to an isodose surface and an isodose surface of a model-generated outcome.

At block 1002, process 1000 can receive a set of clinical goals. The clinical goals can be provided by a practitioner and may include a combination of (potentially conflicting) goals, such as providing high dose to a target structure and low dose to an OAR near to (and possibly overlapping with) the target structure. It is assumed that at least one of the clinical goals is expressed with reference to an isodose surface, such as in the examples of volume limits, dose limits, and isodose surface conformation described above.

At block 1004, for any clinical goal that is expressed with reference to an isodose surface, process 1000 can define a cost function component based directly on the isodose surface, e.g., according to any of Eqs. (1)-(4) above. For clinical goals not expressed with reference to an isodose surface, other definitions of a cost function component can be used, such as DVH-based or gEUD-based definitions.

At block 1006, cost functions and cost function gradients for one or more candidate treatment plans can be computed. Process 1000 allows for multiple clinical goals, each having a corresponding cost function component, and for each cost function component, a corresponding contribution to the cost function gradient can be separately computed. The total cost function for a candidate treatment plan can be defined as the sum of the cost function components corresponding to all of the clinical goals; as noted above, each cost function component can include a weight assigned as part of the optimization process. Similarly, a cost function gradient for a candidate treatment plan can be defined as the sum of a cost function gradient component (also referred to as a "gradient element") corresponding to each clinical goal, where the gradient element corresponding to each clinical goal is determined from the gradient of the corresponding cost function component.

Where a particular clinical goal is expressed with reference to an isodose surface, process 900 (or a similar process) can be used at block 1006 to compute the corresponding gradient element. For any cost function components that are not expressed with reference to an isodose surface, other techniques (e.g., conventional DVH-based techniques or gEUD-based techniques) can be used to compute the corresponding contribution to the cost function gradient. In some embodiments, block 1006 can be repeated for multiple candidate treatment plans. For example, a library (or database) of treatment plans (where each plan specifies a different combination of values of adjustable machine parameters) can be defined for a particular radiation therapy system, and some or all of the plans from the library can be used as candidate treatment plans. The particular selection of candidate treatment plans is not critical to understanding the present disclosure.

At block 1008, cost function minimization can be performed using the computed cost functions and cost function gradients associated with different treatment plans. In some embodiments, each clinical goal is assigned a weight, and the total cost function is defined as a weighted sum of the corresponding contributions to the cost function. Gradient descent methods or other methods can be used to find a minimum of the cost function; a particular technique is not critical to understanding the present disclosure.

At block 1010, an optimized treatment plan can be generated based on the result of cost function minimization at block 1008. In some embodiments, the optimized treatment plan can be the one of the candidate treatment plans for which the value of the cost function is closest to the minimum. In other embodiments, the optimized treatment plan can be determined by interpolating between (or among) two (or more) candidate treatment plans that yield close-to-minimum values of the cost function. Again, a particular technique for generating an optimized treatment plan is not critical to understanding the present disclosure. At block 1012, information about the optimized treatment plan can be presented to the user. For example, a graphical user interface can show a DVH for various volumes of interest and/or a color-coded image showing the dose at various points in space, which may include a rendering of various isodose surfaces. Other information that may be of interest, such as treatment time or particular machine parameters for the optimized treatment plan, can be presented if desired.

In some embodiments, process 1000 can be used in an iterative fashion for user-guided treatment planning. After seeing the information presented at block 1012, the user may make adjustments to the clinical goals and/or to the weights assigned to particular clinical goals. For example, to adjust a clinical goal, the user may be able to operate a graphical user interface to adjust the position of an isodose line directly or to indicate that dose in a particular region should be increased or reduced. Process 1000 can be repeated with the modified clinical goals (and associated weights). Depending on the particular modification to the clinical goals, at block 1004, new components can be added to the cost function to reflect the modification, or components of the cost function can be modified.

Once a (final) optimized treatment plan has been generated, the treatment plan can be used to control operation of radiation treatment system 100 (or radiation treatment system 500) to perform a radiation treatment on the patient. For instance, the optimized treatment plan can include or imply a corresponding set of adjustable machine parameter values that produce the treatment fields of the optimized treatment plan, and in embodiments where process 1000 is implemented in control circuitry 560, control circuitry 560 can be instructed by the user to perform the radiation treatment in accordance with the deliverable plan. In embodiments where process 1000 is implemented on a different computer system, the treatment plan can be represented in a computer-readable format (e.g., a configuration file conforming to a particular syntax) and delivered to control circuitry 560 using any available data-transfer mechanism (e.g., network transfer, removable storage medium). Control circuitry 560 can read and execute the treatment plan. Executing the treatment plan can include operating the beam source, movable gantry, and MLC in accordance with machine parameters specified in the treatment plan to deliver radiation to a patient.

It will be appreciated that the processes described herein are illustrative and that variations and modifications are possible. Blocks or operations described sequentially can be performed in parallel (e.g., computing cost function gradients for multiple voxels or computing cost function components corresponding to different clinical goals), order of blocks or operations can be modified to the extent logic permits, and blocks or operations can be added or omitted. In some embodiments, use of a process such as process 900 can allow an optimization process such as process 1000 to work at sub-voxel accuracy, e.g., by using a level-set presentation for the target structures (or other structures) specifying the target boundary with sub-voxel accuracy. These and similar processes can be applied to treatment planning for a variety of radiation treatment systems including photon-beam and particle-beam systems, and for a variety of treatment modalities including IMRT and VMAT.

6. Computer System Implementation

Figure 11:
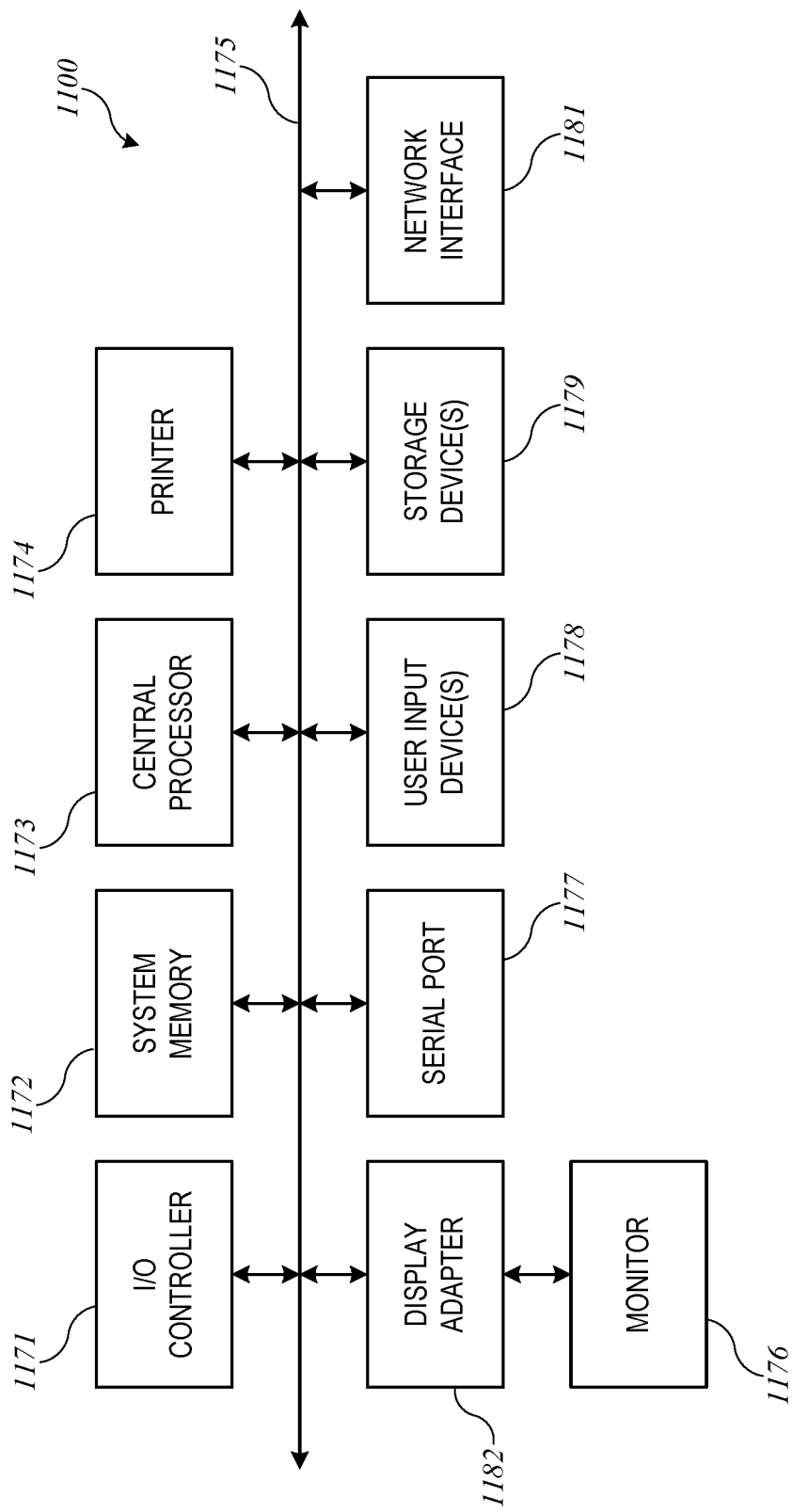
FIG. 11 shows a simplified block diagram of a computer system suitable for use in some embodiments of the present invention.

Processes described herein can be implemented in computer systems of various designs. FIG. 11 shows a simplified block diagram of a computer system 1100 suitable for use in some embodiments of the present invention. Computer system 1100 includes a number of different subsystems interconnected via a system bus 1175. The core subsystems include an input/output (I/O) controller 1171, a system memory 1172 (e.g., DRAM, SRAM, PROM, and/or other computer-readable media), and a central processor 1173. Central processor 1173, which can be implemented using one or more programmable integrated circuits (including single-core and/or multi-core microprocessors) controls operations of computer system 1100 by executing program code that can be stored (at least temporarily) in system memory 1172. Accordingly, central processor 1173 can communicate with each subsystem and can control the execution of instructions from system memory 1172 or storage device(s) 1179, as well as the exchange of information between subsystems. Similarly, any of the data mentioned herein can be delivered from one component to another component and can be output to (or input from) the user. In some embodiments, central processor 1173 may be coupled to one or more coprocessors, such as one or more graphics processing units (not shown) that are designed for high-throughput parallel processing.

I/O controller 1171 allows other components to be communicatively coupled to central processor 1173, and central processor 1173 can receive input from other components and/or send output to other components via I/O controller 1171. Accordingly, additional subsystems such as printer 1174; user input device(s) 1178 (e.g., keyboard, mouse, etc.); storage device(s) 1179 (e.g., various computer-readable media such as hard disk drives or other fixed storage devices, removable disks, removable solid-state memory devices such as USB thumb drives, etc.); monitor 1176, which is coupled to display adapter 1182; and the like may be communicably coupled to central processor 1173. Peripherals and I/O devices, which may couple to I/O controller 1171, can be connected to the computer system using various interconnect standards known in the art, such as serial port 1177. Wireless local-area connectivity (e.g., via Bluetooth or Wi-Fi or the like) may also be supported.

In some embodiments, network interface 1181 may be provided to enable communication between computer system 1100 and other computer systems, e.g., via Ethernet, Wi-Fi, or the like. Network interface 1181 may support connection to a local area network and/or to a wide-area network such as the internet. Thus, for example, processes 900 and 1000 and other processes described herein can be implemented in one instance of computer system 1100, which can communicate treatment plans to another instance of computer system 1100 local to radiation treatment system 100 (e.g., including control circuitry 560).

In some embodiments, computer system 1100 is implemented as a single computer apparatus with some or all of the subsystems described above. In some embodiments, a single instance of computer system 1100 can include multiple instances of the same components or subsystems, e.g., connected together by an internal interface. In some embodiments, two or more instances of computer system 1100 (which can be configured alike or differently as desired) can communicate over a network. In such embodiments, one instance can be considered a client and another instance a server.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing or connecting electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Any of the software-implemented components or functions described in this application may be realized in the form of software code to be executed by a processor; such code may be created using any suitable computer language such as, for example, Java, C++ or Perl using, for example, conventional or object-oriented techniques. The software code may be stored as a series of instructions or commands on a computer readable storage medium; suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may also be a combination of multiple such media. Computer readable storage media encoded with the program code may be packaged with a compatible device or provided separately from other devices (e.g., as a separately packaged computer readable storage medium or via an interne download operation that results in the program code being stored on a computer readable storage medium of the device that downloaded it). Any such computer readable storage medium may reside on or within a single computer product (e.g. a hard drive, a CD, or an entire computer system) and may be present on or within different computer products within a system or network. Such programs may also be encoded and transmitted using carrier signals adapted for transmission via wired, optical, and/or wireless networks conforming to a variety of protocols, including the Internet. (It is noted that "storage" of programs or data is distinct from propagation of programs or data using transitory media such as carrier waves.)

Any of the methods described herein may be totally or partially performed with a computer system including one or more processors, which can be configured to perform the steps or operations. Thus, embodiments of the present invention can include computer systems configured to perform the steps or operations of any of the methods described herein, potentially with different components performing different steps or operations (or different groups of steps or operations).

7. Further Embodiments

While the invention has been described with reference to specific embodiments, those skilled in the art will appreciate that variations and modifications are possible and that specific embodiments described herein are intended as illustrative and not limiting. All processes described herein are illustrative, and variations and modifications are possible. Except where internal logic requires a particular order, operations or blocks described sequentially may be executed in parallel, order of operations may be varied, and operations described in connection with different blocks can be combined. Further, it is not necessary that every operation described herein be performed in every embodiment of the invention; some operations can be omitted, and other operations not specifically described herein may be added. Techniques described herein for determining cost function components and corresponding contributions to a cost function gradient can be applied in a variety of contexts, including but not limited to MCO. The particular definitions of cost function components (and gradients) provided herein are intended as examples, and other definitions that define a cost function component directly by reference to the location of a particular isodose surface can be used in the same manner as the examples described herein.

Thus, while the invention has been described with reference to specific embodiments, it is to be understood that the invention is defined by the following claims.

What is claimed is:

1. A method for radiation treatment planning, the method comprising:
   receiving a set of clinical goals wherein at least a first clinical goal in the set of clinical goals is expressed with reference to a threshold isodose surface corresponding to a threshold dose;
   defining a cost function having a cost function component corresponding to each clinical goal in the set of clinical goals, wherein a first cost function component corresponding to the first clinical goal is defined based directly on the threshold isodose surface;
   computing, for each treatment plan in a set of candidate treatment plans, the cost function and a cost function gradient having a gradient element corresponding to each cost function component, wherein for the first cost function component, computing the gradient element includes:
      identifying a set of voxels of interest, wherein the set of voxels of interest includes at least some voxels that are intersected by the threshold isodose surface, wherein identifying the set of voxels of interest for a particular candidate treatment plan in the set of candidate treatment plans includes computing a dose distribution for the particular candidate treatment plan using a dose prediction model, the dose distribution including a dose at each of a plurality of lattice points, the plurality of lattice points defining a set of voxels having corner points at adjacent lattice points, and identifying, as a voxel of interest, any voxel in the set of voxels for which at least one of the corner points has a dose greater than the threshold dose and the at least one of the corner points has a dose less than the threshold dose;
      computing, for each voxel of interest, a gradient of the dose distribution; and
      determining, for each voxel of interest, a local contribution to the gradient element based at least in part on the gradient of the dose distribution;
   performing a cost function minimization using the cost function and the cost function gradient; and
   generating an optimized treatment plan based on a result of the cost function minimization.

2. The method of claim 1 wherein the set of voxels of interest includes only voxels that are intersected by the threshold isodose surface.

3. The method of claim 1 wherein computing the gradient of the dose distribution for each voxel of interest includes interpolating a dose between the corner points of each voxel of interest.

4. The method of claim 3 wherein the interpolation is a linear interpolation.

5. The method of claim 3 wherein determining the local contribution to the gradient element for each voxel of interest includes:
   using the gradient of the dose distribution to determine a relationship between a change in a portion of a volume of each voxel of interest that lies within the isodose surface and a change in dose; and
   using the determined relationship to compute the local contribution to the gradient element.

6. The method of claim 1 wherein every clinical goal in the set of clinical goals is expressed with reference to a respective threshold isodose surface.

7. The method of claim 1 further comprising:
presenting information about the optimized treatment plan to a user.

8. A method for radiation treatment planning, the method comprising:
receiving a set of clinical goals wherein at least a first clinical goal in the set of clinical goals is expressed with reference to a threshold isodose surface corresponding to a threshold dose;
defining a cost function having a cost function component corresponding to each clinical goal in the set of clinical goals, wherein a first cost function component corresponding to the first clinical goal is defined based directly on the threshold isodose surface;
computing, for each treatment plan in a set of candidate treatment plans, the cost function and a cost function gradient having a gradient element corresponding to each cost function component, wherein for the first cost function component, computing the gradient element includes:
identifying a set of voxels of interest, wherein the set of voxels of interest includes at least some voxels that are intersected by the threshold isodose surface;
computing, for each voxel of interest, a gradient of a dose distribution; and
determining, for each voxel of interest, a local contribution to the gradient element based at least in part on the gradient of the dose distribution;
performing a cost function minimization using the cost function and the cost function gradient;
generating an optimized treatment plan based on a result of the cost function minimization; and
operating a radiation treatment system in accordance with the optimized treatment plan to perform a radiation treatment on a patient.

9. The method of claim 8 wherein the optimized treatment plan includes a control point sequence and a multileaf collimator leaf sequence and wherein operating the radiation treatment system in accordance with the treatment plan includes:
providing, by a treatment head of the radiation treatment system coupled with a radiation source, radiation at one or more angles specified by the control point sequence and using a sequence of movements of a multileaf collimator specified by the multileaf collimator leaf sequence, such that radiation in accordance with the treatment plan is delivered to the patient.

10. A system comprising:
a memory; and
a processor coupled to the memory and configured to:
receive a set of clinical goals wherein at least a first clinical goal in the set of clinical goals is expressed with reference to a threshold isodose surface corresponding to a threshold dose;
define a cost function having a cost function component corresponding to each clinical goal in the set of clinical goals, wherein a first cost function component corresponding to the first clinical goal is defined based directly on the threshold isodose surface;
compute, for each treatment plan in a set of candidate treatment plans, the cost function and a cost function gradient having a gradient element corresponding to each cost function component, wherein for the first cost function component, computing the gradient element includes:
identifying a set of voxels of interest, wherein the set of voxels of interest includes at least some voxels that are intersected by the threshold isodose surface, wherein identifying the set of voxels of interest for a particular candidate treatment plan in the set of candidate treatment plans includes computing, for each voxel of interest, a gradient of a dose distribution, and determining, for each voxel of interest, a local contribution to the gradient element based at least in part on the gradient of the dose distribution;
perform a cost function minimization using the cost function and the cost function gradient; and
generate an optimized treatment plan based on a result of the cost function minimization.

11. The system of claim 10 wherein the set of voxels of interest includes only voxels that are intersected by the threshold isodose surface.

12. The system of claim 10 wherein the processor is further configured such that computing the gradient of the dose distribution for each voxel of interest includes interpolating a dose between corner points of each voxel of interest.

13. The system of claim 12 wherein the interpolation is a linear interpolation.

14. The system of claim 12 wherein the processor is further configured such that determining the local contribution to the gradient element for each voxel of interest includes:
using the gradient of the dose distribution to determine a relationship between a change in a portion of a volume of each voxel of interest that lies within the isodose surface and a change in dose; and
using the change in volume to compute the local contribution to the gradient element.

15. The system of claim 10 wherein every clinical goal in the set of clinical goals is expressed with reference to a respective threshold isodose surface.

16. The system of claim 10 wherein the processor is further configured to:
present information about the optimized treatment plan to a user.

17. The system of claim 10 wherein the processor is further configured to:
operate a radiation treatment system in accordance with the optimized treatment plan to perform a radiation treatment on a patient.

18. The system of claim 17 further comprising:
a treatment head coupled with a radiation source; and
a multileaf collimator,
wherein the processor is further configured such that operating the radiation treatment system in accordance with the optimized treatment plan includes providing, by the treatment head, radiation from the radiation source at one or more angles specified by the optimized treatment plan and using a sequence of movements of the multileaf collimator specified by the optimized treatment plan, such that radiation in accordance with the optimized treatment plan is delivered to the patient.

* * * * *